United States Patent [19]

Yokota et al.

[11] Patent Number: 4,625,063

[45] Date of Patent: Nov. 25, 1986

[54] PRODUCTION OF TERTIARY AMINE

[75] Inventors: Yukinaga Yokota, Osaka; Yuji Sawamoto, Wakayama; Hideki Taniguchi, Wakayama; Kazuhiko Okabe, Wakayama, all of Japan

[73] Assignee: Kao Corporation, Tokyo, Japan

[21] Appl. No.: 741,979

[22] Filed: Jun. 6, 1985

[30] Foreign Application Priority Data

Jun. 29, 1984 [JP] Japan ................................. 59-134447

[51] Int. Cl.$^4$ ........................ C07C 85/06; C07C 85/08
[52] U.S. Cl. ..................................... 564/480; 564/473
[58] Field of Search .............................. 564/480, 473

[56] References Cited

U.S. PATENT DOCUMENTS

| | | | |
|---|---|---|---|
| 2,636,051 | 4/1953 | Whetstone et al. | 564/473 |
| 3,068,232 | 12/1962 | Moss | 564/480 |
| 4,197,260 | 4/1980 | Siclari et al. | 564/473 |
| 4,209,424 | 6/1980 | Le Goff et al. | 564/480 |

FOREIGN PATENT DOCUMENTS

| | | |
|---|---|---|
| 2535073 | 2/1977 | Fed. Rep. of Germany . |
| 19604 | 2/1977 | Japan . |
| 55-704 | 11/1981 | Japan . |
| 663294 | 12/1951 | United Kingdom ................ 564/473 |

*Primary Examiner*—Charles F. Warren
*Assistant Examiner*—R. A. Picard
*Attorney, Agent, or Firm*—Flynn, Thiel, Boutell & Tanis

[57] ABSTRACT

A tertiary amine of a high purity is prepared from an alcohol or an aldehyde and a primary or second amine at a low temperature, using a catalyst of copper, nickel and an element belonging to the VIII platinum group such as platinum, palladium, ruthenium and rhodium, while removing out water formed by the reaction.

6 Claims, No Drawings

PRODUCTION OF TERTIARY AMINE

The present invention relates to a process for producing a tertiary amine by reacting an alcohol or an aldehyde with a primary or secondary amine.

Aliphatic tertiary amines are substances having industrial importance as intermediates of, for example, rust preventives, surfactants, bactericides, dyeing aids for textiles, and softeners. Further, tertiary amines produced from polyhydric alcohols are substances which are important as urethane catalysts.

DESCRIPTION OF PRIOR ART

A process for producing an amine by reacting the corresponding alcohol or aldehyde with ammonia, a primary amine or a secondary amine is well known. However, it was difficult to obtain a particular amine, especially, a tertiary amine selectively by reacting an alcohol or the like with an amine or the like.

Processes for producing a tertiary amine from an alcohol and an amine are reported in, for example, Japanese Patent Laid-Open No. 19604/1977 (copper chromite catalyst, cobalt catalyst), Japanese Patent Laid-Open No. 59602/1978 (copper/molybdenum, copper/tungsten catalyst), U.S. Pat. No. 3,223,734 (Raney nickel catalyst, copper chromite catalyst), and German Patent Laid-Open No. 1,493,781 (supported nickel catalyst, supported cobalt catalyst). However, these catalysts are unsatisfactory in respect of activity and selectivity, and because they are used in a large amount, the yield of the desired tertiary amine is low.

A process described in Japanese Patent Publication No. 55704/1982 is one developed to solve these problems. This process is one comprising obtaining the desired tertiary amine in high yields by using a copper/nickel bimetallic catalyst.

However, the reaction by this catalyst is not necessarily satisfactory. That is to say, although the catalyst activity in this process is better than that of other ordinary processes, the activity is sometimes lowered markedly as the reaction temperature is lowered because they show a marked reaction temperature dependency. It is sometimes necessary to raise the reaction temperature or increase the amount of a catalyst added depending on the kind of alcohol. Such a procedure has a disadvantage that by-products which are undesirable for the quality of a tertiary amine are apt to form and the yields of the desirable tertiary amine is decreased. In order to obtain a high-quality tertiary amine in high yields, it is necessary that the catalyst can catalyze a reaction at a lower temperature, can exhibit high activity with a small amount, and has a high selectivity.

SUMMARY OF THE INVENTION

As a result of extensive studies to solve the problems of a copper/nickel catalyst, the inventors of the present invention have developed a novel trimetallic catalyst comprising copper, nickel, and a small amount of Group VIII noble metal, and have succeeded in solving these problems by one effort. Namely, aiming at enhancing the activity and selectivity of a catalyst by improving the ability of dehydrogenation and hydrogenation required for the catalyst in producing a tertiary amine by reacting an alcohol or an aldehyde with an amine, the inventors of the present invention have made a search for new functions and properties by intermetallic combination among copper, nickel and a third metal species.

As a result, the inventors of the present invention have found a new function of showing high activity and selectivity with a small amount, which has not been attained with a copper/nickel bimetallic system, by a combination effect among copper, nickel, and a Group VIII noble metal by using a catalyst metal composition comprising copper, nickel and a Group VIII noble metal as a third metallic component.

Namely it has been found, as a result of the search for new functions by combining copper with nickel and a third metallic component, that Group VIII noble metals, especially, platinum, palladium, ruthenium, and rhodium, can exhibit an extremely effective function as a third metallic component for the reaction of the present invention. Especially, third metallic components such as Group VIII noble metals only can exhibit new functions when combined with copper and nickel, while the addition of other third metallic components such as chromium, iron, zinc, zirconium, manganese, or cobalt could show no effect, but rather brought about a decrease in the function of a catalyst. The present invention is based on a finding that new catalyst properties which can not be obtained in any other metallic compositions can be attained only by an interaction among copper, nickel and a Group VIII platinum metal third metallic component.

Namely, the present invention provides a process for producing a tertiary amine in high yields by reacting an alcohol or an aldehyde with a primary or secondary amine, characterized by using a copper/nickel/Group VIII noble metal catalyst, effecting the reaction at a temperature of 150° to 250° C. and a pressure of atmospheric pressure to 5 atm (gauge) in the presence of this catalyst, while removing the water formed by the reaction continuously or intermittently from the system.

According to the process of the present invention, because the catalyst is highly active, the reaction condition is mild and the reaction can be carried out in relatively simple equipment and completed within a short time with a very small amount of a catalyst. In addition, the catalyst of the present invention can show a catalyst activity which is several times higher than that of the copper/nickel catalyst described in the above mentioned Japanese Patent Publication No. 55704/1982 and has an extremely excellent reaction selectivity. It is thus possible to obtain a desired tertiary amine in high yields and with a high quality, because little side reactions occur. Further, the combination of copper with nickel and a Group VIII noble metal third component has a feature that it can increase the durability of the formed catalyst as compared with conventional catalysts and that the loss of the catalyst activity is scarcely observed even after the catalyst is recovered and reused several to several tens of times.

Because the catalyst of the present invention can show higher activity and selectivity than those of conventional catalysts, and permits a reaction at low temperatures and atmospheric pressure, a necessary amount of the catalyst can be decreased and the selectivity can be improved. Therefore, it becomes possible to produce a high-quality tertiary amine in high yields even from a branched aliphatic alcohol or aldehyde from which the corresponding tertiary amine could not be obtained by conventional techniques. Further, it has becomes possible to produce a tertiary amine in remarkably high yields also from polyhydric alcohols from which the production of tertiary amines is difficult from the viewpoint of the yields and qualities of the tertiary amines produced because side reactions are apt to occur.

The catalyst to be used in the present invention contains copper, nickel and a Group VIII noble metal as essential components, and the ratio of copper and nickel to a Group VIII noble metal in the catalyst metal composition can be selected arbitrarily.

Namely, the molar ratio of copper to nickel is preferably within the range of 1:9 to 9:1 (in terms of metal atoms), and the amount of a Group VIII noble added is preferably within the range of 0.001 to 0.1 (by molar ratio) to the total of copper and nickel.

Group VIII noble metals particularly suited for the present reaction are platinum, palladium, ruthenium, and rhodium.

The three components of copper, nickel and a Group VIII noble metal are essential to a catalyst metal composition, and catalysts suitable in the present invention can be selected from a variety of forms.

Namely, in the present invention, only when the three components of copper, nickel, and a Group VIII noble metal are present as a catalyst composition in the reaction system, the effect of an interaction among these components can be realized, these components have an essential catalyst function and the catalyst activity in the reaction of an alcohol with an amine can be developed only when each metallic component is reduced in a hydrogen atmosphere. Therefore, any difference in the form of the metals before reduction and in the state of the system after the reduction is not particularly limited in the present invention, and it is only necessary that the form is one which allows the catalyst to exhibit an interaction among copper, nickel and a Group VIII noble group metal when they are reduced in a hydrogen atmosphere in the process described in the present invention.

Therefore, the forms of the metals suitable for the process of the present invention include (1) forms which can be dispersed in a reaction medium, such as metals themselves, oxides, hydroxides, etc., thereof, and mixtures thereof, (2) forms which can be dispersed in a reaction medium, such as a mixture of copper, nickel, and a Group VIII noble metal each supported on a suitable carrier, and three components of copper, nickel, and a Group VIII noble metal uniformly supported on the same carrier, (3) forms which form metal colloids to form a homogeneous system in a reaction system, such as aliphatic carboxylic acid salts of these metals, and their complexes stabilized with suitable ligands, and (4) a mixture of forms (1) and (2) which forms a dispersion in a reaction medium and form (3) which becomes homogeneous in a reaction medium, and forms which are dispersions before hydrogen reduction and become homogeneous after hydrogen reduction.

It is only necessary that the three metallic components essential to the present invention can produce an interaction among the three components by reduction in a hydrogen atmosphere.

A catalyst in a form more desirable for the process of the present invention is one obtained by uniformly supporting these metallic components on a suitable carrier, from the viewpoint of stabilization of catalyst metals, i.e., fixation of active surfaces, and resistance to catalyst poisons.

Carriers suitable for supporting the three metallic components of copper, nickel, and a Group VIII noble metal of the present invention are those which are generally used as catalyst carriers, such as alumina, silica/alumina, diatomaceous earth, silica, active carbon, and natural and synthetic zeolites. Although the amounts of the catalyst metals supported on a carrier may be selected arbitrarily, they are usually within the range of 5 to 70%.

A method for supporting these three metallic components on the surface of a carrier can be selected from a variety of methods. In this case, the forms of the metals of a catalyst material may be oxides or hydroxides of copper, nickel or a Group VIII noble metal, or various metal salts thereof. For example, chlorides, sulfates, nitrates, acetates and aliphatic carboxylic acid salts of copper, nickel, or a Group VIII noble metal, or complexes of these metals, such as acetylacetone complexes and dimethylglyoxime complexes of copper, nickel, or a Group VIII noble metal, and further carbonyl complexes, amine complexes, phosphine complexes, etc. of Group VIII noble metals can be used. When the catalyst is produced by a method comprising supporting these metallic materials on a support, any of the following well-known methods can be used: a method comprising placing a carrier in a solution of suitable salts of copper, nickel and a Group VIII noble metal, fully impregnating the carrier with the solution, and drying and calcining the carrier (impregnation method), a method comprising placing a carrier in an aqueous solution of suitable salts of copper, nickel, and a Group VIII noble metal, for example, an aqueous solution of copper sulfate, nickel nitrate, and a chloride of a platinum metal and, after sufficient mixing, precipitating the metal salts on the carrier by adding an aqueous alkali solution such as an aqueous sodium carbonate solution, an aqueous sodium hydroxide solution or ammonia water (coprecipitation method), a method comprising performing ion exchange between sodium, potassium, or the like and copper, nickel, and a Group VIII noble metal on a zeolite (ion exchange method), and a method comprising melting copper, nickel, a Group VIII noble metal, and aluminum metal by heating, solidifying the melt into an alloy by cooling, and dissolving the aluminum in the alloy with caustic soda (alloy method). In cases of the impregnation method and the coprecipitation method, the carrier is fully washed with water after precipitation of metals, dried near 100° C., and calcined at 300° to 700° C. to obtain a catalyst.

Further, a method is also effective which comprises supporting copper alone or together with nickel on a carrier by a method such as above, before using in a reaction, adding supported nickel or Group VIII noble metal, or an aliphatic carboxylic acid salt or complex, and combining copper and nickel with the platinum metal in a reaction medium in a hydrogen atmosphere.

A catalyst form in which the three components are uniformly supported on the same carrier is more desirable.

In this invention, these three components of copper, nickel, and a Group VIII noble metal are essential, and as regards the addition of a metal other than these three components, a small amount of a metal can not exert any effect on the change in the properties of these three metallic components, and a large amount of a metal adversely affects an interaction of the three metallic components, which is not desirable.

Further, it has been found that the reaction of the present invention is adversely affected when any of the three components of the catalyst composition of the present invention is absent.

The alcohols or aldehydes which are starting materials of the present invention are straight or branched, saturated or unsaturated, aliphatic alcohols or aldehydes of 8 to 36 carbon atoms and include alcohols such as octyl alcohol, lauryl alcohol, myristyl alcohol, stearyl alcohol, behenyl alcohol, oleyl alcohol, or mixtures thereof, Ziegler alcohols obtained by the Ziegler process, oxo alcohols obtained by the oxo synthesis, branched alcohols such as Guerbet alcohols, and aldehydes such as laurylaldehyde, oxoaldehyde, and other aldehydes corresponding to the above-mentioned alcohols.

Further, a variety of polyhydric alcohols can be used. For example, polyhydric alcohols such as 1,3-butanediol, 1,4-butanediol, 1,5-pentanediol, diethylene glycol, and triethylene glycol can be mentioned. Other alcohols including aromatic alcohols such as benzyl alcohol, polyoxy ether alcohols such as aliphatic alcohol/ethylene oxide or propylene oxide adduct, and amino alcohols such as ethanolamine and diethanolamine can be mentioned.

Particularly preferable alcohols and the aldehydes include aliphatic alcohols and aldehydes selected from among saturated or unsaturated, straight or branched, aliphatic alcohols and aldehydes of 8 to 36 carbon atoms and aliphatic glycols of 2 to 12 carbon atoms. Examples of the amines which are reacted with these alcohols or aldehydes are primary amines such as monomethylamine, ethylamine, and dodecylamine, and secondary amines such as dimethylamine, diethylamine, and didodecylamine.

In this invention, it is an essential requirement to remove the water formed by the reaction of an alcohol or an aldehyde with an amine from the system. If the formed water is not removed from the system, the performance of the catalyst of the present invention can not be fully exhibited. Namely, the activity and selectivity of the catalyst are too low to obtain a tertiary amine easily in high yields. For example, when dimethylamine is used as the amine and the reaction is carried out without removing the formed water, the amount of a secondary amine formed as a by-product which is difficultly separable from a tertiary amine merely by distillation, such as a monoalkylmethylamine, is increased and high-boiling substances such as condensed aldehyde are formed in quantity, so that the yields of the desired tertiary amine are decreased.

The removal of water may be performed intermittently or continuously during the reaction and it is necessary that the formed water be suitably removed before it stays long in the reaction system. It is preferable that the water be removed continuously as soon as it is formed. In practice, it is a usual practice that a suitable amount of hydrogen gas is introduced into the reaction system during the reaction and the formed water and excess amine are expelled together with the hydrogen gas, and it is also possible to recirculate the hydrogen gas after condensing and separating the formed water in a condenser. It is also possible to remove the formed water by azeotropically distilling it with a suitable solvent previously added to the reaction system.

Although a catalyst prereduced with hydrogen gas separately may be used in the process of the present invention, a non-reduced catalyst may be fed in a reaction vessel together with an alcohol or an aldehyde as a reactant and reduced by heating it to a reaction temperature while introducing hydrogen gas alone or as a mixture with a small amount of gaseous amine. Namely, the copper/nickel/Group VIII noble metal catalyst of the present invention is markedly featured in that it can be reduced during the course of heating it to the reaction temperature because it has a low reduction temperature.

An embodiment of the process of the present invention will be described briefly.

An alcohol or an aldehyde and a catalyst are fed in a reaction vessel equipped with a tube for introducing hydrogen and an amine, and a condenser and a separator for condensing and separating the water formed from the reaction, excess amine and an oily distillate. Although the catalyst may be used in any desired amount, it is usually within the range of 0.1 to 2% by weight, based on the alcohol or aldehyde charge, because the catalyst of the present invention is highly active. After purging the system with nitrogen gas, the heating of the reaction mixture is started while introducing hydrogen alone or as a mixture with a small amount of a gaseous amine. Although the reaction temperature is usually 180 to 230° C., it may be outside this range, depending upon the kind of a reaction. The catalyst is reduced and brought to an active state during this heating. After reaching a predetermined temperature, an amine is fed to start the reaction. During the reaction, the formed water is discharged together with gaseous substances (hydrogen and excess amine) and a small amount of an oily distillate from the reaction system and passed through the condenser and the separator, where the oily distillate is separated. The separated oily mass is recirculated to the reaction vessel. On the other hand, an analysis of the gaseous substances (hydrogen and excess amine) revealed that it was substantially free of by-products (for example, hydrocarbons, amine by-products formed by the disproportionation of the starting amine, etc.), thus verifying a high selectivity of the catalyst of the present invention. Thus it was found that the gaseous substances can be recycled by using a circulator without any purification step. After the reaction, the product is separated from the catalyst by distilling the reaction mixture as such (as in the case of a tertiary amine with one long-chain alkyl), or by filtering it (as in the case of a tertiary amine with two long-chain alkyls). The tertiary amine obtained by the filtration can be distilled into an extremely pure form.

PREFERABLE EMBODIMENT OF THE INVENTION

The present invention will now be described in more detail with reference to examples and comparative examples.

EXAMPLE 1 AND COMPARATIVE EXAMPLES 1 AND 2

A trimetallic copper/nickel/Group VIII noble metal catalyst supported on synthetic zeolite was prepared as follows.

A 1-l flask was charged with synthetic zeolite and then with a solution formed by dissolving copper nitrate, nickel nitrate and ruthenium chloride in water at a molar ratio of Cu:Ni:Ru of 4:1:0.01, and the mixture was heated with stirring. After the temperature of the reaction mixture reached 90° C., a 10% aqueous $Na_2CO_3$ solution was slowly added dropwise, while controlling the pH at 9 to 10. After one hour aging, the precipitate was filtered, washed with water, dried at 80° C. for 10 hours, and calcined at 600° C. for 3 hours. The amount of the metal oxides supported on the catalyst was 50% based on the carrier.

Next, an alcohol was reacted with dimethylamine by using the above-produced catalyst. For comparison, similar reactions were carried out by using a bimetallic copper/nickel catalyst and a bimetallic copper/Group VIII noble metal catalyst, each prepared in a similar manner.

300 g of stearyl alcohol and 1.5 g (0.5% based on the alcohol) of the above catalyst were fed in a 1-l flask equipped with a condenser and a separator for separating the water formed by the reaction and agitated. After purging the system with nitrogen gas, the reaction mixture was heated.

When the temperature of the reaction mixture reached 100° C., hydrogen gas was introduced through a flow meter into the system at a flow rate of 10 l/h, and the reaction mixture was heated to 190° C. While the reaction mixture was being kept at 190° C., a gas mixture of dimethylamine and hydrogen was blown into the reaction system at a flow rate of 40 l/h, and the reaction was followed up by means of amine values and gas chromatography.

The results are shown in Table 1.

The results are shown in Table 2.

TABLE 2

| Run No. | Catalyst*1 third metallic component | Reaction time (hour) | Product composition (wt. %) | | |
|---|---|---|---|---|---|
| | | | un-reacted alcohol | stearyl-dimethyl-amine | miscella-neous |
| Comp. Ex. 3 | Fe | 10 | 4.9 | 65.4 | 29.5 |
| Comp. Ex. 4 | Zn | 10 | 6.0 | 71.0 | 23.0 |
| Comp. Ex. 5 | Zr | 10 | 0.6 | 76.7 | 22.5 |
| Comp. Ex. 6 | Cr | 10 | 40.2 | 24.5 | 22.1 |
| Ex. 2 | Pt | 4 | 4.0 | 91.3 | 4.7 |
| Ex. 3 | Pd | 4 | 5.4 | 90.3 | 4.3 |
| Ex. 4 | Rh | 4 | 5.1 | 85.2 | 9.7 |
| Ex. 1 | Ru | 4 | 2.5 | 91.0 | 6.5 |
| Comp. Ex. 1 | nil | 10 | 5.7 | 89.0 | 5.3 |

*1Cu/Ni/third component ratio = 4/1/0.01 amount of supported catalyst = 50%
Reaction conditions:
alcohol: stearyl alcohol
amine: dimethylamine
reaction temperature: 190° C.
amount of catalyst added: 0.5 wt. % based on alcohol The results show that, in the production of a monoalkyldimethylamine by the reaction of stearyl alcohol with dimethylamine, the catalyst systems containing iron, zinc, zirconium, chromium, or the like as a third

TABLE 1

| Run No. | Catalyst composition | molar ratio among metals | Amount of metal added (ppm*) | | | Reaction time (hour) | Composition (wt. %) | | |
|---|---|---|---|---|---|---|---|---|---|
| | | | Cu | Ni | Ru | | unreacted alcohol | stearyl-dimethyl-amine | miscella-neous |
| Ex. 1 | Cu/Ni/Ru | 4/1/0.01 | 2000 | 500 | 5 | 4 | 2.5 | 91.0 | 6.5 |
| Comp. Ex. 1 | Cu/Ni | 4/1 | 2000 | 500 | — | 4 | 20.3 | 75.6 | 4.1 |
| | | | | | | 10 | 5.7 | 89.0 | 5.3 |
| Comp. Ex. 2 | Cu/Ru | 4/0.04 | 2000 | — | 20 | 10 | 55.2 | 38.7 | 6.1 |

*based on alcohol

These results show that, as compared with the conventional bimetallic Cu/Ni catalyst system (Comp. Ex. 1), the trimetallic Cu/Ni/Group VIII noble metal (Ru) catalyst system of the present invention could show such a high activity that the reaction time was shortened to about a half or below and the alcohol conversion was also high when only 5 ppm, based on alcohol, of a Group VIII noble metal was added to the reaction system.

It was also found that the bimetallic catalyst system comprising copper and a platinum metal (except Ni, Comp. Ex. 2) had an activity lower than that of the bimetallic Cu/Ni catalyst system and could exhibit a high activity only when it was used in the form of a trimetallic Cu/Ni/Group VIII noble metal (Ru) catalyst system.

EXAMPLES 2 TO 4 AND COMPARATIVE EXAMPLES 3 TO 6

The effect of a copper/nickel/third metal component catalyst was examined by the same reaction as in Example 1. The kind of the third metallic component in the catalyst was varied. The third metallic component catalyst was prepared in the same manner as in Example 1.

metallic components showed markedly worsened reaction selectivity than the conventional bimetallic copper/nickel catalyst (Comp. Ex. 1), and by-products were increased. On the other hand, it is also shown that the catalyst systems formed by adding a Group VIII noble metal (platinum, palladium, rhodium, or ruthenium) as a third metallic component to Cu/Ni did not show worsened reaction selectivity, but showed a reaction activity at least twice higher than that of the bimetallic Cu/Ni catalyst.

The above results demonstrate that when a Group VIII noble metal as a third metallic component is added to copper/nickel, the resulting catalyst can show a markedly high activity in the reaction by virtue of an interaction among the three metallic components of copper, nickel, and a platinum metal.

EXAMPLES 5 AND 6 AND COMPARATIVE EXAMPLES 7

An investigation was made about the synthesis of a dialkylmethylamine by reacting a straight-chain alcohol with a monomethylamine by using the catalyst of the present invention. The catalysts were prepared in the same manner as in Example 1. The results are shown in Table 4.

TABLE 4

| Run No. | Catalyst composition (molar ratio) | Reaction time (hour) | Product composition (wt. %) | | |
|---|---|---|---|---|---|
| | | | unreacted alcohol | didecyl-monomethyl-amine | miscellaneous |
| Ex. 5 | Cu/Ni/Ru = 4/1/0.01 | 5.0 | 1.0 | 91.7 | 7.3 |
| Ex. 6 | Cu/Ni/Pd = 4/1/0.04 | 5.0 | 0.3 | 92.8 | 6.9 |
| Comp. Ex. 7 | Cu/Ni = 4/1 | 10.5 | 5.0 | 88.5 | 6.5 |

Conditions:
reaction temperature: 200° C.
alcohol: decyl alcohol
amount of catalyst added: 1 wt. % based on alcohol These results show that the catalysts of the present invention were useful also in the reaction of an alcohol with a primary amine (monomethylamine), and could allow one to produce a corresponding tertiary amine with high activity and selectivity.

EXAMPLES 7 TO 10 AND COMPARATIVE EXAMPLE 8

A branched oxo alcohol was reacted with monomethylamine in the same manner as in Example 1 by using a highly active trimetallic copper/nickel/Group VIII noble metallic catalyst which is the catalyst of the present invention.

The alcohol used was on oxo alcohol comprising a mixture of alcohols having 12 to 13 carbon atoms and a branched-chain alcohol content of 94% (straight-chain alcohol content of 6%). The catalyst was produced in the same manner as in Example 1.

The results are shown in Table 5.

TABLE 5

| Run No. | Catalyst composition*1 | Reaction time (hour) | Product composition (wt. %) | |
|---|---|---|---|---|
| | | | tert. amine*2 | miscellaneous*3 |
| Ex. 7 | Cu/Ni/Ru | 6.0 | 91.9 | 8.1 |
| Ex. 8 | Cu/Ni/Pd | 6.0 | 92.6 | 7.4 |
| Ex. 9 | Cu/Ni/Pt | 8.0 | 90.1 | 9.9 |
| Ex. 10 | Cu/Ni/Rh | 8.0 | 90.2 | 9.8 |
| Comp. Ex. 8 | Cu/Ni | 12.0 | 74.8 | 25.2 | reaction temperature: 230° C.
amount of catalyst added: 1.0 wt. % based on alcohol
*1molar ratio among metal atoms; copper:nickel:platinum metal = 8:2:0.08
*2dialkylmonomethylamine
*3unreacted alcohol and by-products The above results show that, when a dialklyl-monomethyl amine was syntensized by the reaction of a branched alcohol (oxo alcohol) with monomethylamine, the conventional bimetallic Cu/Ni catalyst system gave a low yield of a tertiary amine and a large amount of by-products formed even after a prolonged reaction time, because of its low activity and selectivity. Owing to the influence of steric hindrance, a catalyst having a high activity is necessary for the production of a tertiary amine from a branched alcohol.

On the other hand, it was found that, because of its remarkably high activity, the trimetallic Cu/Ni/Group VIII noble metal catalyst can allow one to produce the desired branched tertiary amine in high yields within a short time.

EXAMPLES 11 TO 14

An investigation was made about the effect of the catalyst of the present invention on the synthesis of a tertiary amine by the reaction of an alcohol or an aldehyde with dimethylamine.

In the preparation of the catalysts, a Group VIII noble metal component (5% palladium supported on active carbon or ruthenium in the form of dodecacarbonyltriruthenium) was combined with supported copper/nickel in a hydrogen atmosphere in a reaction medium.

The results are shown in Table 6.

TABLE 6

| Run No. | Alcohol or aldehyde | Catalyst*3 | | Reaction temperature (°C.) | Reaction time (hour) | Composition (wt. %) | | |
|---|---|---|---|---|---|---|---|---|
| | | composition | amount (%) | | | tert. amine | unreacted alcohol | miscellaneous |
| Ex. 11 | oxo alcohol*1 | Cu/Ni/Pd | 0.5 | 200 | 7 | 92.4*4 | 4.6 | 3.0 |
| Ex. 12 | Guerbet alcohol*2 | Cu/Ni/Pd | 1.0 | 230 | 6 | 70.0*5 | 24.0 | 6.0 |
| Ex. 13 | 1,6-hexanediol | Cu/Ni/Ru | 0.5 | 190 | 5 | 90.8*6 | 5.8 | 3.4 |
| Ex. 14 | laurylaldehyde | Cu/Ni/Ru | 0.5 | 190 | 3 | 91.1*7 | 5.0 | 3.9 |

*1oxo alcohol: a mixture of 12-13 C alcohols, with a branched-chain alcohol content of 21% (straight-chain alcohol content of 79%)
*2Guerbet alcohol: a branched-chain alcohol (total carbon atoms of 28) of the formula: $R'-\underset{\underset{R''}{|}}{CH}-CH_2OH$
*3Cu/Ni/platinum metal molar ratio = 4/1/0.01. The amount is based on alcohol or aldehyde.
*4 and *5 in terms of monoalkyldimethylamine
*6in terms of N,N,N',N'—tetramethylhexamethylenediamine
*7in terms of lauryldimethylamine The above results show that the catalysts of the present invention could allow one to produce tertiary amines in high yields and remarkably high selectivity also in the reaction of a branched alcohol, a polyhydric alcohol (glycol) or an aldehyde as a starting material with a secondary amine.

Although, side reactions such as decomposition or condensation, of a starting material usually increase when such a branched alcohol, polyhydric alcohol or aldehyde is used as the starting material, it has been demonstrated that the catalyst having the composition of the present invention is extremely excellent one that can serve to solve the problem.

EXAMPLE 15

The catalyst was recovered by filtration from the reaction mixture after the reaction in Example 1, and the amination reaction was repeated under the same condition. The results are shown in Table 7.

TABLE 7

| Times of repetition | Reaction time (hour) | Product composition (wt. %) | | |
|---|---|---|---|---|
| | | unreacted alcohol | stearyldi-methylamine | miscellaneous |
| 1 | 4 | 2.5 | 91.0 | 6.5 |
| 2 | 4 | 1.1 | 92.2 | 6.7 |
| 3 | 4 | 0.5 | 93.1 | 6.4 |
| 4 | 4 | 0.6 | 93.6 | 5.8 |
| 5 | 4 | 0.8 | 93.5 | 5.7 |

The embodiments of the invention in which an exclusive property or privilege is claimed are defined as follows:

1. A process for manufacturing a tertiary amine, which comprises the steps of reacting an alcohol or an aldehyde with a primary amine or a secondary amine, in the presence of a catalyst of copper metal, nickel metal and an element belonging to the Group VIII noble metals of the Periodic Table, at a temperature of 150° to 250° C., at a pressure in the range of from atmospheric pressure to 5 atmospheres, while removing out the water formed by the reaction, and separating the obtained tertiary amine.

2. A process as claimed in claim 1, in which said element of the Group VIII noble metals is platinum, palladium, ruthenium or rhodium.

3. A process as claimed in claim 1, in which the molar ratio of copper to nickel in said catalyst is in the range of 1:9 to 9:1 and the molar ratio of the Group VIII noble metal to the sum of copper and nickel is in the range of 0.001 to 0.1.

4. A process as claimed in claim 1, in which the catalyst is supported on a carrier in an amount of 5 to 70 wt. %.

5. A process for the preparation of a tertiary amine, which comprises reacting (1) an alcohol or an aldehyde selected from the group consisting of aliphatic alcohols having 8 to 36 carbon atoms, aldehydes having 8 to 36 carbon atoms, polyether alcohols, aliphatic glycols having from 2 to 12 carbon atoms, amino alcohols and aromatic alcohols, with (2) a primary or secondary amine selected from the group consisting of primary aliphatic amines and secondary aliphatic amines, at a temperature of from 150° to 250° C. and a pressure of from atmospheric pressure up to 5 atmospheres gauge pressure, in the presence of from 0.1 to 2.0 wt. %, based on said alcohol or aldehyde, of a catalyst, said catalyst consisting of nickel metal, copper metal and a Group VIII noble metal selected from the group consisting of Pt, Pd, Ru and Rh, said catalyst being supported on an inert solid carrier, wherein the mole ratio of nickel metal:copper metal is from 90:10 to 10:90, the mole ration of (a) said Group VIII noble metal to (b) the sum of copper metal plus nickel metal is from 0.001 to 0.1, and the amount of nickel metal plus copper metal plus Group VIII noble metal is fron 5 to 70 wt. %, based on the weight of said carrier, while removing water formed during the reaction from the reaction system, and then recovering the tertiary amine.

6. A process for the preparation of a tertiary amine, which comprises placing in a reaction vessel (1) an alcohol or an aldehyde selected from the group consisting of aliphatic alcohols having 8 to 36 carbon atoms, aldehydes having from 8 to 36 carbon atoms, polyether alcohols, aliphatic glycols having from 2 to 12 carbon atoms, amino alcohols and aromatic alcohols, and (2) from 0.1 to 2.0 wt. %, based on said alcohol or aldehyde, of a catalyst, said catalyst consisting of nickel metal, copper metal and a Group VIII noble metal selected from the group consisting of Pt, Pd, Ru and Rh, said catalyst being supported on an inert solid carrier wherein the mole ratio of nickel metal:copper metal is from 10:90 to 90:10, the mole ratio of (a) said Group VIII noble metal to (b) the sum of copper plus nickel is from 0.001 to 0.1 and the amount of nickel metal plus copper metal plus Group VIII noble metal is from 5 to 70 wt. %, based on the weight of said carrier, then replacing the atmosphere in said reaction vessel with nitrogen, then blowing hydrogen gas through the contents of said reaction vessel while raising the temperature of said contents to a temperature in the range of 180° to 230° C. whereby to reduce the catalyst, then at said temperature blowing into the contents of said vessel a mixture of hydrogen gas and a gas of a primary or secondary amine selected from the group consisting of primary aliphatic amine and secondary aliphatic amines, at a pressure in said reaction vessel of from atmospheric pressure up to five atmospheres gauge pressure and removing from said reaction vessel a gaseous stream of hydrogen, unreacted amine and water formed by the reaction of said amine with said alcohol or aldehyde whereby to obtain a reaction mixture containing a tertiary amine, and then distilling said reaction mixture to recover said tertiary amine.

* * * * *